United States Patent [19]

Chang et al.

[11] Patent Number: 5,726,114
[45] Date of Patent: Mar. 10, 1998

[54] METHOD OF PREPARATION OF EX SITU SELECTIVATED ZEOLITE CATALYSTS FOR ENHANCED SHAPE SELECTIVE APPLICATIONS AND METHODS TO INCREASE THE ACTIVITY THEREOF

[75] Inventors: Clarence D. Chang, Princeton; John D. Lutner, Hamilton Square, both of N.J.; Sharon B. McCullen, Newton, Pa.; Paul G. Rodewald, Rocky Hill; David S. Shihabi, Pennington, both of N.J.

[73] Assignee: Mobil Oil Corporation, Fairfax, Va.

[21] Appl. No.: 516,435

[22] Filed: Aug. 17, 1995

Related U.S. Application Data

[63] Continuation of Ser. No. 141,758, Oct. 27, 1993, abandoned.
[51] Int. Cl.$^6$ ..................................... B01J 29/06
[52] U.S. Cl. .......................... 502/64; 502/63; 502/71; 502/77
[58] Field of Search .................... 502/63, 64, 71, 502/77

[56] References Cited

U.S. PATENT DOCUMENTS

| | | |
|---|---|---|
| 3,257,310 | 6/1966 | Plank et al. . |
| 3,437,587 | 4/1969 | Elbert et al. . |
| 3,657,151 | 4/1972 | Noble ........................... 502/62 |
| 3,682,996 | 8/1972 | Kerr . |
| 3,698,157 | 10/1972 | Allen et al. . |
| 4,016,218 | 4/1977 | Haag et al. . |
| 4,060,568 | 11/1977 | Rodewald . |
| 4,086,287 | 4/1978 | Kaeding et al. . |
| 4,090,981 | 5/1978 | Rodewald . |
| 4,100,215 | 7/1978 | Chen . |
| 4,117,024 | 9/1978 | Kaeding . |
| 4,117,026 | 9/1978 | Haag et al. . |
| 4,127,616 | 11/1978 | Rodewald . |
| 4,145,315 | 3/1979 | Rodewald . |
| 4,224,141 | 9/1980 | Morrison et al. . |
| 4,283,306 | 8/1981 | Herkes . |
| 4,326,994 | 4/1982 | Haag et al. . |
| 4,402,867 | 9/1983 | Rodewald . |
| 4,443,554 | 4/1984 | Dessau . |
| 4,451,572 | 5/1984 | Cody ........................... 502/62 |
| 4,465,886 | 8/1984 | Rodewald . |
| 4,477,583 | 10/1984 | Rodewald . |
| 4,487,843 | 12/1984 | Telford et al. . |
| 4,522,929 | 6/1985 | Chester et al. . |
| 4,528,276 | 7/1985 | Cambell et al. ........................... 502/62 |
| 4,548,914 | 10/1985 | Chu . |
| 4,559,314 | 12/1985 | Shihabi . |
| 4,843,057 | 6/1989 | D'Amore et al. . |
| 4,851,604 | 7/1989 | Absil et al. . |
| 4,927,979 | 5/1990 | Yamagishi et al. . |
| 4,950,835 | 8/1990 | Wang et al. . |
| 5,173,461 | 12/1992 | Absil et al. . |
| 5,349,113 | 9/1994 | Chang et al. ........................... 585/475 |
| 5,349,114 | 9/1994 | Lago et al. ........................... 585/475 |
| 5,365,003 | 11/1994 | Chang et al. ........................... 585/475 |
| 5,365,004 | 11/1994 | Beck et al. ........................... 585/475 |
| 5,367,099 | 11/1994 | Beck et al. ........................... 585/475 |
| 5,403,800 | 4/1995 | Beck et al. ........................... 502/64 |

FOREIGN PATENT DOCUMENTS

0 296 582 A2  6/1988  European Pat. Off. .

OTHER PUBLICATIONS

Nakajima et al., "p-Xylene-Selective Disproportionation of Toluene over a Modified Pentasil Type Zeolite", *Sekiyu Gakkaishi*, 35(2), 185–189 (1992).
Hibino et al., "Shape-Selectivity over HZSM-5 Modified by Chemical Vapor Deposition of Silicon Alkoxide", *Journal of Catalysis*, 128, 551–558 (1991).
Kono et al., "Regioselective Hydrogenation Using Platinum-Support Zeolite Modified by CVD-Method", *Bull. Chem. Soc. Jpn.*, 64, 2508–2512 (1991).

*Primary Examiner*—Michael Lewis
*Assistant Examiner*—Thomas G. Dunn, Jr.
*Attorney, Agent, or Firm*—Peter W. Roberts; Malcolm D. Keen

[57] ABSTRACT

A method of preparing a modified catalytic molecular sieve for enhanced shape selective hydrocarbon conversions in which a catalytic molecular sieve is modified by being exposed to at least one ex situ selectivation sequence, each sequence including an impregnation of the molecular sieve with a selectivating agent in an aqueous emulsion and a subsequent calcination of the impregnated molecular sieve. The selectivating agent compositions for the ex situ selectivation method are also described, including the selectivating agents, the surfactants, and the aqueous components. Also, a method for moderate steaming of the ex situ selectivated molecular sieve. Also a method for in situ trim-selectivating the ex situ selectivated catalytic molecular sieve. Also described is the modified catalytic molecular sieve modified by this method. Also described is a process for shape selective hydrocarbon conversion comprising contacting a hydrocarbon feedstream under conversion conditions with the modified catalytic molecular sieve.

14 Claims, No Drawings

METHOD OF PREPARATION OF EX SITU SELECTIVATED ZEOLITE CATALYSTS FOR ENHANCED SHAPE SELECTIVE APPLICATIONS AND METHODS TO INCREASE THE ACTIVITY THEREOF

This is a continuation of copending application(s) Ser. No. 08/141,758 filed on Oct. 27, 199, now abandoned.

BACKGROUND OF THE INVENTION

The present invention relates to a modified catalytic molecular sieve and a method for its modification. The invention also relates to shape selective hydrocarbon conversion processes over a modified catalyst.

The term "shape-selective catalysis" describes unexpected catalytic selectivities in zeolites. The principles behind shape selective catalysis have been reviewed extensively, e.g., by Chen et al., "Shape Selective Catalysis in Industrial Applications" 36 Marcel Dekker, Inc. (1989) Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective alkyl-substituted benzene disproportionation to para-dialkyl-substituted benzene.

A representative para-dialkyl substituted benzene is para-xylene. The production of para-xylene is typically performed by methylation of toluene or by toluene disproportionation over a catalyst under conversion conditions. Examples include the reaction of toluene with methanol, as described by Chen et al., *J. Am. Chem. Soc.*, 101, 6783 (1979), and toluene disproportionation, as described by Pines in *The Chemistry of Catalytic Hydrocarbon Conversions*, Academic Press, N.Y., p 72 (1981). Such methods typically result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

The equilibrium reaction for the conversion of toluene to xylene and benzene proceeds as follows:

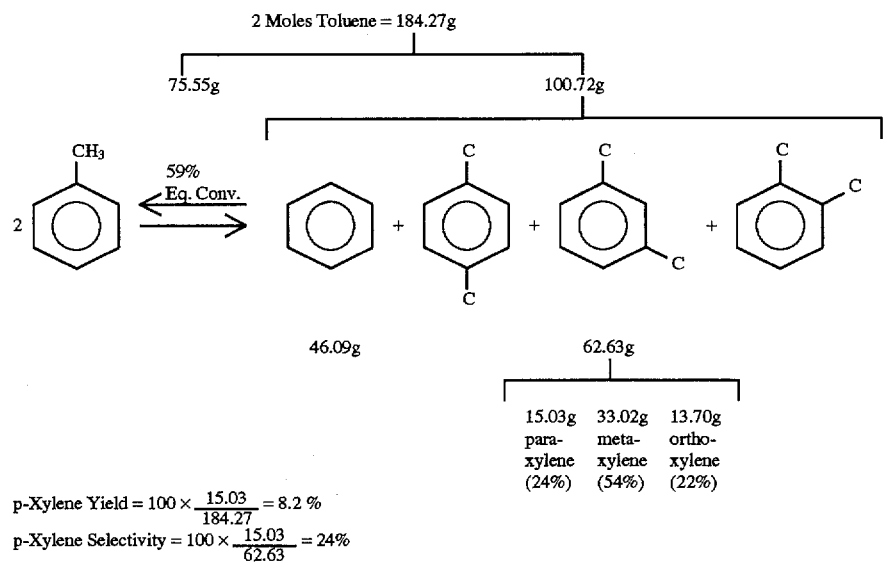

p-Xylene Yield = $100 \times \frac{15.03}{184.27} = 8.2\%$ p-Xylene Selectivity = $100 \times \frac{15.03}{62.63} = 24\%$ Various methods are known in the art for increasing the para-selectivity of zeolite catalysts. One such method is to modify the catalyst by treatment with a "selectivating agent". For example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568 and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

A publication by Kuno et al., "Regioselective Hydrogenation Using Platinum-Support Zeolite Modified by CVD-Method", *Bull. Chem. Soc. Jpn.*, 64, 2508–2512 (1991), describes multiple chemical vapor deposition (CVD) of tetraethoxysilane (i.e., tetraethylorthosilicate) on zeolite to improve selectivity of hydrogenation of unsaturated compounds. Another CVD method, described in U.S. Pat. No. 4,950,835, employs CVD of tetraethyl-orthosilicate in either a continuous or a pulsed mode in situ to improve selectivity of alkylbenzene conversions.

Historically, ex situ selectivation of zeolites has involved single applications of the modifying compound. It may be noted, however, that a suggestion of multiple treatments was made in U.S. Pat. No. 4,283,306. This patent discloses the promotion of crystalline silica catalyst by application of a silica source such as tetraethylortho-silicate. The '306 patent contrasts the performance of catalyst treated once with a tetraethylorthosilicate solution followed by calcination against the performance of catalyst treated twice with tetraethylorthosilicate and calcined after each treatment. The '306 disclosure shows that the twice-treated catalyst is less active and less selective than the once-treated catalyst as measured by methylation of toluene by methanol, indicating that multiple ex situ selectivation confers no benefit and in fact reduces a catalyst's efficacy in shape-selective reactions.

U.S. Pat. No. 4,060,568 describes a zeolite modification method that includes exposing a zeolite to a volatile silane that preferably enters the pores of the zeolite, hydrolyzing the silane with ammonia, and calcining the treated zeolite. The patent describes a catalyst modified by three such treatments, but provides no description of any enhancement in catalytic selectivity or activity over that which might follow from a single such treatment.

There has been no suggestion, however, that the efficiency of silicon deposition on a zeolite can be enhanced by the use of multiple ex situ impregnations of zeolite with a silicon compound. Nor has there been any suggestion that multiple ex situ treatments of zeolite with a silicon compound can improve the selectivity and activity of zeolites in shape selective hydrocarbon conversion processes.

Various organic compounds have been employed as carriers for silicon compounds in the silicon impregnation methods applied to zeolite catalysts. For example, U.S. Pat. Nos. 4,145,315, 4,127,616, and 4,090,981 describe the use of inter alia $C_{5-7}$ alkanes as solvents for silicon impregnation. U.S. Pat. No. 4,060,568, describes the use of silicon compounds for zeolite modification but without a carrier for the silicon compound.

Alternatively, U.S. Pat. No. 4,402,867 describes the use of aqueous dispersions of silicon-containing compounds for the deposition of silica on molecular sieves. The silicon-containing compounds used in this patent are preferably of a size so as to allow silica entry into the pores of the zeolite and thereby to modify the catalyst for enhanced shape selectivity in certain hydrocarbon conversions. The aqueous emulsions are described as being contacted with the molecular sieves at a temperature of between about 10° C. and about 200° C., for about 0.2 to about 5 hours, and then calcined in an oxygen-containing atmosphere.

There has been no suggestion, however, of the use of surfactants to enhance the preparation of aqueous emulsions of silicon compounds as compositions useful for silicon impregnation of zeolites. Nor has there been any suggestion that the selectivation of zeolites by one or more ex situ impregnations of zeolites with aqueous emulsions of silicon compounds, followed by calcination after each impregnation, would improve the selectivity and activity of the catalysts.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

But there has been no suggestion of the use of moderate steaming to improve the selectivity and activity of catalysts modified by multiple impregnations of emulsified silicon compounds.

Therefore, it would be a significant advance in the art to overcome the difficulties, disadvantages, and deficiencies associated with conventional methods for modifying catalytic molecular sieves, the molecular sieves modified by those methods, and the processes of shape selective hydrocarbon conversions using those modified catalytic molecular sieves.

The present invention solves the difficulties, disadvantages, and deficiencies inherent in the prior art by providing an improved method of modifying catalytic molecular sieves, improved selectivating agent compositions useful for modifying catalytic molecular sieves, improved modified catalytic molecular sieves, and improved processes for shape selective hydrocarbon conversions.

It has now been found that a multiple impregnation scheme provides unexpectedly better results in shape-critical hydrocarbon conversions than single silicon impregnation pre-treatment schemes.

It has also now been found that a multiple impregnation scheme provides unexpectedly more efficient deposition of the silicon compound on the catalyst than single silicon impregnation schemes.

In addition, it has now been found that aqueous emulsions of silicon compounds, prepared and stabilized through the use of surfactants, and, having the advantages of ease and safety of industrial application, unexpectedly provide results that are at least substantially equivalent to those achieved by employment of conventional zeolite modification methods.

Furthermore, it has also now been found that a multiple silicon impregnation scheme for zeolite catalyst selectivation followed by steam treatment produces additional unexpectedly better results than the multiple impregnation treatment alone.

Accordingly, it is a purpose of the invention to provide an improved method of silicon deposition on a zeolite for enhancing shape selectivity of the zeolite in hydrocarbon conversion processes.

It is also a purpose of the invention to provide an improved modified catalytic molecular sieve for shape selective hydrocarbon conversion processes.

It is another purpose of the invention to provide improved aqueous emulsions of organosilicon compounds, and thereby to improve the ease with which silicon impregnation of zeolite catalysts may be achieved as well as to improve the safety of such methods.

It is still another purpose of the invention to improve shape selectivity in hydrocarbon conversion processes over molecular sieves by providing modified molecular sieves having improved activity and shape selectivity.

SUMMARY OF THE INVENTION

These and other purposes and goals are achieved by the present invention which provides an improved method for modifying a catalytic molecular sieve, improved selectivating agent compositions for modifying catalytic molecular sieves, an improved modified catalytic molecular sieve, and improved shape selective hydrocarbon conversion processes over a modified catalytic molecular sieve.

In one aspect, the modification method includes exposing the catalytic molecular sieve to at least one ex situ selectivation sequence. Each selectivation sequence includes impregnating the catalytic molecular sieve with an emulsified selectivating agent, followed by calcination after each impregnation. Preferably the catalyst is exposed to between about 2 and about 6 ex situ selectivation sequences.

Selectivating agents useful in the present invention include a large variety of silicon-containing compounds, preferably silicon polymers emulsifiable in aqueous media. The emulsions of the invention generally include the emulsifiable selectivating agent, a surfactant, and an aqueous component. The surfactants useful for the invention include ionic and non-ionic surfactants.

In another embodiment the invention is also a method for further modifying a multiply impregnated catalytic molecular sieve by steaming the molecular sieve at moderate temperatures.

In another embodiment the invention also includes a method for further modifying the modified catalytic molecular sieve by in situ trim-selectivating the modified catalytic molecular sieve. The in situ trim-selectivating may be performed by coke trim-selectivating wherein an organic compound is decomposed in the presence of the modified catalytic molecular sieve, at conditions suitable for decomposing the organic compound. Alternatively, the trim-selectivating may be performed by exposing the modified catalytic molecular sieve to a reaction stream that includes a hydrocarbon to be converted and a trim-selectivating agent selected from a group of compounds including a large variety of silicon-containing compounds, at reaction conditions.

The invention is also the modified catalytic molecular sieves modified according to the various embodiments of the method of the invention.

The invention further includes a process for enhanced shape selective conversion of hydrocarbons, involving contacting a hydrocarbon stream, under conversion conditions, with a catalytic molecular sieve that has been modified according to the invention. Preferably, the invention provides a process for enhanced shape selective production of dialkyl-substituted benzenes by contacting a reaction stream comprising an alkylbenzene, under conversion conditions, with a modified catalytic molecular sieve modified according to the invention.

Advantageously, the modified catalyst has enhanced shape selectivity for para-dialkyl-substituted benzene production. Accordingly, the disproportionation process of the invention exhibits increased selectivity for p-dialkylbenzene and may exhibit an increased alkylbenzene disproportionation rate constant.

Other purposes and advantages of the present invention will be more fully apparent from the following detailed disclosure, the scope of which is defined in the appended claims.

DETAILED DESCRIPTION OF THE INVENTION

The present invention relates to a modified catalytic molecular sieve for shape selective hydrocarbon conversions, compositions for modifying a catalytic molecular sieve, a method of preparation of the modified catalytic molecular sieve, and shape selective hydrocarbon conversion processes using the modified catalytic molecular sieve.

The catalytic molecular sieves useful according to the invention preferably include intermediate pore zeolites. It is also preferred that the catalytic molecular sieves of the invention exhibit a Constraint Index of between about 1 and about 12. The method for determining Constraint Index is described fully in U.S. Pat. No. 4,016,218, the disclosure of which is incorporated by reference herein. Zeolites which conform to the specified values of Constraint Index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. An especially preferred zeolite is ZSM-5. Such zeolites are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,640,849, 4,046,685, 4,175,114, 4,199,556, 4,341,748, 3,308,069 and Re. No. 28,341, to which reference is made for the details of these zeolites. The catalytic molecular sieves useful for the invention are preferably in the hydrogen form ("as synthesized") prior to modification, but may be used in the ammonium or sodium form.

The crystal size of zeolites used for the invention is preferably greater than about 0.1 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size was computed by applying the diffusion equation given by J. Crank, "The Mathematics of Diffusion" Oxford at the Clarendon Press, 1957, pp 52–56, for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{03}$, the time required for the uptake of 30% of capacity of hydrocarbon is:

$$d = 0.0704 \times t_{03}^{1/2}$$

In the present case, these measurements have been made on a computer controlled, thermogravimetric electrobalance, but there are numerous ways one skilled in the art could obtain the data.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in the *Journal of Catalysis*, 4, 522–529 (1965); 6, 278 (1966); 61, 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts", *Nature*, 309, 589–591, (14 Jun. 1984)). The experimental conditions of the test used herein include a constant temperature of 538° C. and a variable flow rate as described in detail in the *Journal of Catalysis*, 61, 395 (1980). The catalyst in the present invention has an alpha value greater than 1, for example, from about 1 to about 5000, preferably from about 1 to about 2000. The alpha value of the catalyst may be increased by initially treating the catalyst with nitric acid or by mild steaming before pre-selectivation. This type of steaming is discussed in U.S. Pat. No. 4,326,994, the disclosure of which is incorporated by reference herein.

The silica to alumina ratio ($SiO_2/Al_2O_3$) of the catalysts of the invention may be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 10,000 are useful, it is preferred to use zeolites having ratios of at least about 20 to about 2000.

For the improved disproportionation process of this invention, the suitable molecular sieve may be employed in combination with a support or binder material such as, for example, a porous inorganic oxide support or a clay binder. While the preferred binder is silica, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 30% to about 98% by weight and is preferably from about 50% to about 80% by weight of the composition. The composition may be in the form of an extrudate, beads or fluidizable microspheres. The catalyst may be incorporated with binder either before or after being modified according to the invention.

The catalyst may also include a hydrogenation/dehydrogenation function such as an added metal. While platinum is a preferred metal, other metals of Groups IB to VIII of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.001% to about 2%, typically about 0.5%. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The catalyst can then be filtered, washed with water and calcined at temperatures of from about 250° C. to about 500° C.

While in conventional methods a silicon compound may be employed in the form of a solution, a liquid, or a gas under the conditions of contact with a zeolite, in the method of the invention the silicon compound is preferably in the form of an emulsion. The deposited silicon compound extensively covers, and resides substantially exclusively on, the external surface of the molecular sieve. Examples of the variety of methods of depositing silicon on the surface of the zeolite are found in U.S. Pat. Nos. 4,090,981, 4,127,616, 4,465,886 and 4,477,583, the disclosures of which are incorporated by reference herein. Further examples of the deposition of a silicon compound on zeolite surfaces are described in Nakajima et al., *Sekiyu Gakkaishi*, 35, 185–189 (1992), and in U.S. Pat. No. 4,950,835.

In the modification method of the present invention, a zeolite, either incorporated with a binder or in unbound form, is contacted at least once with a selectivating agent. The selectivating agent comprises a compound or polymer containing a main group or transition metal, preferably silicon. The catalyst is contacted with an emulsified organosilicon selectivating agent, at a catalyst/selectivating agent weight ratio of from about 100/1 to about 1/100, at a temperature of from about 10° C. to about 200° C., at a pressure of from about 0 psig to about 200 psig, for a time of from about 0.1 hr to about 48 hours. The molecular sieve may be contacted with the emulsion either through immersing the molecular sieve in the emulsion or through recirculating the emulsion through a bed of catalyst. The contacted catalyst may then be dried, e.g., by decantation or evaporation of the residual liquid. The catalyst is then calcined. This methodological sequence is termed a "selectivation" sequence. While the catalyst may be exposed to a single selectivation sequence and thereby achieve significant improvement in selectivity and activity, it is preferred that the catalyst be modified by more than one selectivation sequence, preferably by between 2 and 6 selectivation sequences.

The emulsions of the invention include a selectivating agent or a mixture of selectivating agents in an amount of from about 2.5wt. % to about 50wt. %, preferably from about 5 wt. % to about 35 wt. %, under conditions of contact with the catalytic molecular sieve. The emulsions also contain a surfactant or a mixture of surfactants in an amount of from about 0.01 wt. % to about 5 wt. %, preferably from about 0.05 wt. % to about 2 wt. %, under selectivating conditions.

It has been found that a multiple selectivation scheme provides unexpectedly increased efficiency of deposition of the silicon compound on the surface of the catalyst. This increased efficiency allows for the use of relatively small quantities of the emulsified silicon compound as well as relatively small quantities of the aqueous component (aqueous phase). Accordingly, the amount of silica deposited on the catalyst, as a proportion of the silicon compound in the emulsion unexpectedly tends to be greater when the deposition is sequential than when the deposition is made in one impregnation of the catalyst. In addition, it has been unexpectedly observed that the activity and selectivity of the catalyst modified by multiple selectivation sequences tend to be substantially higher than the activity and selectivity of a catalyst modified by the deposition of a comparable amount of silica in a single step.

As was described above, the catalysts of the present invention are ex situ selectivated by one or more coatings with a high efficiency para-selectivating agent, each coating followed by calcination, and the catalyst optionally trim-selectivated with additional high efficiency para-selectivating agent. As used wherein, the term "high efficiency para-selectivating agent" is used to indicate substances that increase the para-selectivity of a catalytic molecular sieve to the stated levels in alkylbenzene disproportionation while maintaining commercially acceptable levels of alkylbenzene to dialkylbenzene conversion. Such substances include, for example, organic silicon ("organosilicon") compounds such as phenylmethyl silicione, dimethyl silicone, and blends thereof which have been found to be suitable. In general, such organosilicon compounds must be emulsifiable in aqueous systems. In addition, "emulsion" is intended to mean a fluid including, a microscopically heterogenous mixture of two normally immiscible substances. A skilled artisan Will appreciate that emulsions differ from solutions, both ideal and colloidal.

Useful selectivating agents include siloxanes which can be characterized by the general formula:

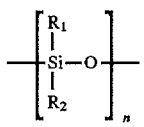

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxy silanes, such as tetramethoxy silane, may also be utilized. These useful silicon-containing selectivating agents include silanes characterizable by the general formula:

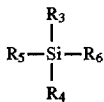

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

Preferred silicon-containing selectivating agents include dimethylphenylmethyl polysiloxane (e.g., DC-550) and phenylmethyl polysiloxane (e.g., DC-510 and DC-710). DC-510, DC-550 and DC-710 are available from Dow Chemical Co., Midland, Mi.

Preferably, the kinetic diameter of the high efficiency, p-xylene selectivating agent is larger than the zeolite pore diameter, in order to avoid entry of the selectivating agent into the pore and any accompanying reduction in the internal activity of the catalyst.

Although aqueous silicone emulsions are commercially available, they may contain significant amounts of added organic materials, such as toluene, for improving stability. The presence of such additional organics increases the complexity, hazards, and cost of zeolite selectivation. Such emulsions are therefore useful, but not preferred, in accordance with the catalyst modification methods of the present invention. With proper formulation, the inventors have succeeded in producing stable emulsions containing a silicone oil, an aqueous component, and a surfactant, while substantially devoid of other components.

The preferred, stable aqueous emulsions of silicone oil are generated by mixing the oil and an aqueous component in the presence of a surfactant or surfactant mixture. Surfactants useful for the present invention include any of a large variety of surfactants, including ionic and non-ionic surfactants. Preferred surfactants include non-nitrogenous non-ionic surfactants such as alcohol, alkylphenol, and poly-alkoxyalkanol derivatives glycerol esters, polyoxyethylene esters, anhydrosorbitol esters, ethoxylated anhydrosorbitol esters, natural fats, oils, waxes and ethoxylated esters thereof, glycol esters, polyalkylene oxide block co-polymer surfactants, poly(oxyethylene-co-oxypropylene) non-ionic surfactants, and mixtures thereof. More preferred surfactants include surfactants having the formula α-[4-(1,1,3,3-tetramethylbutyl)phenyl]ω-hydroxypoly(oxy-1,2-ethanediyl) (Octoxynols), most preferably octoxynol-9. Such preferred surfactants include the TRITON® X series, such as TRITON® X-100 and TRITON®X-305, available from Rohm & Haas Co., Philadelphia, Pa., and the Igepal CA series from GAF Corp., New York, N.Y. Emulsions formulated using such surfactants are effective for selectivating zeolites to enhance shape selectivity, and to passivate surface acidity detrimental to product selectivity in certain regioselective catalytic applications such as the disproportionation of alkylbenzenes.

The aqueous component suitable for use in an emulsion of the invention will substantially constitute the continuous phase of the emulsion. The aqueous component is preferably water. Most preferably, the water is distilled prior to use in the emulsions. Alternatively, the aqueous component may include water and a compound selected from the group including inorganic salts, alcohols having between 1 and 18 carbons, glycols, ethers, neutral or charged sulfoxides, neutral or charged amines, aldehydes, ketones, thiophenes, furans, pyrroles, and mixtures thereof.

Following each deposition of the silicon compound, the catalyst is calcined to decompose the molecular or polymeric species to a solid state species. The catalyst may be calcined, at a rate of from about 0.2° C./minute to about 5° C./minute, to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any selectivation sequence need not be identical, but may vary with respect to the temperature, the rate of temperature rise, the atmosphere, and the duration of calcination.

Factors upon which the amount of silica incorporated with the zeolite is dependent include temperature of contact with the selectivating agent, concentration of the silicon compound in the carrying medium, the degree to which the zeolite has been dried prior to contact with the silicon compound, and conditions (e.g., atmosphere, temperature) of calcination of the zeolite.

After the selectivation procedure, the catalyst may be subjected to steam treatment under moderate conditions. Such conditions include a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours.

The selectivated molecular sieve catalyst, with or without binder, can show improved selectivity upon steaming. Alternatively, excessive steaming can be detrimental to a selectivated catalyst.

According to the process of the invention, an alkylbenzene may be fed simultaneously with a second selectivating agent and hydrogen at reaction conditions until the desired p-dialkylbenzene selectivity, e.g., 90%, is attained, whereupon the co-feed of selectivating agent is discontinued. This co-feeding of selectivating agent with alkylbenzene is a type of "trim-selectivation". Reaction conditions for this type of trim-selectivation step generally include a temperature of from about 350° C. to about 650° C. and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20.

The second selectivating agent for trim-selectivation may be selected from among the exemplary silicon compounds discussed in greater detail above. For example, organic silicon compounds such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., alkylbenzene and hydrogen, are fed in the amounts set forth above. The selectivating agent is fed in an amount of from about 0.001 wt. % to about 10 wt. % of the alkylbenzene according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica to on the catalyst. During the selectivation procedure the para-selectivity of the catalyst will be observed to increase further. The silicon-containing polymer or molecular species may be dissolved in toluene, ethylbenzene or other appropriate aromatic or hydrocarbon carrier.

Alternatively, the catalyst, prior to contacting with alkylbenzene under disproportionation conditions, may be subjected to "trim-selectivation" by being exposed to a thermally decomposable organic compound at an elevated temperature in excess of the decomposition temperature of said compound but below the temperature at which crystallinity of the zeolite is adversely affected. Generally, this temperature will be less than about 650° C. This type of trim-selectivation is known as "coke trimming".

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, preferably the alkylbenzene being subjected to disproportionation itself. In the latter case, the alkylbenzene is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the alkylbenzene feed is continued in contact with the coke-containing catalyst under conditions of temperature and hydrogen concentration conducive to disproportionation, with a greatly reduced coking rate.

While not wishing to be bound by theory, it is believed that the advantages of the present invention are in part obtained by rendering acid sites on the external surfaces of the catalyst substantially inaccessible to reactants, while increasing catalyst tortuosity. Acid sites existing on the external surface of the catalyst are believed to isomerize the solution-phase p-dialkylbenzene back to an equilibrium level with the other two dialkylbenzene isomers, in the case of xylenes thereby reducing the amount of p-xylene in the xylenes product to only about 24%. By reducing the availability of these acid sites to the solution-phase p-dialkylbenzene, the relatively high proportion of the para isomer can be maintained. It is believed that the high-efficiency, p-dialkylbenzene selectivating agents of the present invention block or otherwise render these external acid sites unavailable to the p-dialkylbenzene by chemically modifying said sites.

Disproportionation of Alkyl-Substituted Benzenes

Zeolites modified in accordance with the invention are generally useful as catalysts in shape selective hydrocarbon conversion processes including: cracking reactions involving dewaxing of hydrocarbon feedstocks; isomerization of alkylaromatics; oligomerization of olefins to form gasoline, distillate, lube oils or chemicals; alkylation of aromatics; transalkylation of alkylaromatics; conversion of aromatics to dialkyl-substituted benzenes; conversion of oxygenates to hydrocarbons; rearrangement of oxygenates; and conversion of light paraffins and olefins to aromatics.

Zeolites modified in accordance with the invention are particularly useful for shape selective disproportionation of alkyl-substituted benzenes to yield dialkyl-substituted benzenes. The modified zeolite catalysts of the invention are advantageously used in the conversion of alkylbenzene compounds to provide dialkylbenzene products which are highly enriched in the para-dialkylbenzene isomer. Conversion reactions of this type include alkylation, transalkylation and disproportionation of alkylbenzenes. Alkylations of aromatics in which the catalysts of the invention can be used are described, for example, in U.S. Pat. Nos. 3,755,483, 4,086,287, 4,117,024 and 4,117,026, which are incorporated herein by reference.

The modified catalysts of the present invention have been found to be particularly useful in the selective production of para-dialkyl-substituted benzenes containing alkyl groups of 1 to 4 carbon atoms, such as para-xylene. Such processes are typified by the disproportionation, in the presence of the modified catalyst, of a hydrocarbon precursor, typically a monoalkyl-substituted benzene having 1 to 4 carbon atoms in the alkyl substituent.

As described in U.S. Pat. No. 3,755,483, aromatic hydrocarbons such as benzenes, naphthalenes, anthracenes and substituted derivatives thereof, e.g., toluene and xylene, may be alkylated with alkylating agents such as olefins ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psia, a mole ratio of aromatic/alkylating agent of from about 1:1 to about 20:1, and a weight hourly space velocity (WHSV) of 20 to 3000 $hr^{-1}$ over ZSM-12 which is a ZSM-5 type catalyst.

As described in U.S. Pat. No. 4,086,287, monoalkylbenzenes having alkyls of 1–2 carbons, such as toluene and ethylbenzene, may be ethylated to produce a para-ethyl derivative, e.g., para-ethyltoluene at a temperature of from about 250° C. to about 600° C., a pressure of 0.1 atmospheres to 100 atmospheres, a WHSV of 0.1 to 100 hr$^-$, and a ratio of feed/ethylating agent of 1 to 10 over a catalyst having an acid activity, i.e., alpha, of 2 to 5000, modified by pre-coking or combining with oxides of phosphorus, boron or antimony to attain a catalyst with a xylene sorption capacity greater than 1 g/100 g of zeolite and an ortho xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 describes a process for the ethylation of toluene or ethylbenzene to produce p-ethyltoluene at a temperature of 350° C. to 550° C., a critical pressure of greater than one atmosphere and less than 400 psia, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

U.S. Pat. No. 4,117,026 describes the production of para-dialkyl benzenes having alkyls of 1 to 4 carbons under conditions which vary according to the feed. When the feed includes monoalkyl-substituted benzenes having an alkyl group of 1 to 4 carbons, olefins of 2 to 15 carbons, or paraffins of 3 to 60 carbons or mixtures thereof, conversion conditions include a temperature of 250° C. to 750°, a pressure of 0.1 to 100 atmospheres and a WHSV of 0.1 to 2000 hr$^{-1}$. For the disproportionation of toluene, the conditions include a temperature of 400° C. to 700° C., a pressure of 1 to 100 atmospheres and a WHSV of 1 to 50 hr$^{-1}$. When the feed includes olefins of 2 to 15 carbons including cyclic olefins, the conversion conditions include a temperature of 300° C. to 700° C., a pressure of 1 to 100 atmospheres and a WHSV of 1 to 1000 hr$^{-4}$. When the feed includes paraffins of 3 to 60 carbons, conditions include a temperature of 300° C. to 700° C., a pressure of 1 to 100 atmospheres and a WHSV of 0.1 to 100 hr$^{-1}$. However, for lower paraffins of 3 to 5 carbons, the temperature should be above 400° C. When the feed includes mixed aromatics such as ethylbenzene and toluene, and also optionally olefins of 2 to 20 carbons or paraffins of 5 to 25 carbons, conversion conditions include a temperature of 250° C. to 500° C. and a pressure greater than 200 psia. In the absence of added aromatics, the olefins and higher paraffins are more reactive and require lower severity of operation, e.g., a temperature of 250° C. to 600° C., preferably 300° C. to 550° C.

In general, therefore, catalytic conversion conditions over a catalyst comprising a modified zeolite include a temperature of from about 100° C. to about 760° C., a pressure of from about 0.1 atmosphere (bar) to about 200 atmospheres (bar), a weight hourly space velocity of from about 0.08 to about 2000 hr$^{-1}$, and a hydrogen/organic, e.g., hydrocarbon compound, mole ratio of from 0 to about. 100.

Toluene Disproportionation

The present invention is described in detail below in relation to the disproportionation of alkyl-substituted benzenes, such as toluene and ethylbenzene, over a multiply-selectivated and optionally steamed catalyst. Normally a single pass conversion of an alkylbenzene stream results in a product stream which includes dialkylbenzenes having alkyl groups at all locations, i.e., o-, m-, and p-dialkylbenzenes. A catalyst treated in the manner described herein exhibits a desirable decreased ortho-dialkylbenzene sorption rate parameter and yields a significantly para-selected product from alkylbenzene disproportionation. For example, diffusion rate constants in toluene disproportionation have been discussed by Olson et al., "Structure-Selectivity Relationship in Xylene Isomerization and Selective Toluene Disproportionation", *Catalytic Materials: Relationship Between Structure and Reactivity*, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$. For high selectivity and catalyst efficiency it is desirable to have:

$$k_D \ll D_T/r^2.$$

The degree of para-selectivity depends on the activity and the diffusion characteristics of the catalyst. The primary product will be rich in the para isomer if initially produced m- and o-xylene diffuse out of the zeolite crystal at a rate ($D_{m,o}/r^2$) that is lower than that of their conversion to p-xylene ($k_1$), as well as lower than that of the p-xylene diffusion ($D_p/r^2$) out of the catalyst, where:

$D_m$=diffusion of m-xylene;

$D_o$=diffusion of o-xylene;

$D_p$=diffusion of p-xylene;

r=length of diffusion path (crystal size);

$k_x$=rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_l > D_{m,o}/r^2.$$

In such a case the rate of conversion of m- and o-xylenes to p-xylene exceeds the diffusivities of the m- and o-xylenes. As a result, the p-xylene proportion of the xylene yield will be increased. Those skilled in the art will appreciate that similar considerations apply to the diffusivities of other alkylbenzenes.

The invention also comprises a process for near regioselective conversion of alkylbenzene to para-dialkylbenzene by disproportionating alkylbenzene in a reaction stream containing an alkylbenzene feed with a selectivated and optionally steamed catalytic molecular sieve, optionally in the presence of hydrogen, and at reaction conditions suitable to provide p-dialkylbenzene selectivity of greater than about 80%, preferably greater than 90%. The production stream may also contain small amounts of o- and m-dialkylbenzene and trace amounts of impurities.

As used herein, the term "para-dialkylbenzene selectivity" or "para-selectivity" refers to the proportion of p-dialkylbenzene, indicated as a percentage, among all of the dialkylbenzene products of the reaction, i.e., p-dialkylbenzene, o-dialkylbenzene, and m-dialkylbenzene. Those skilled in the art will appreciate that the relative proximity of the boiling points of these isomers necessitates relatively expensive separation processes for the isolation of p-dialkylbenzene. On the other hand, p-dialkylbenzenes are more readily separated from other components in the product stream such as benzene, monoalkylbenzenes and other alkyl-substituted benzenes.

Furthermore, the dialkylbenzenes are known to proceed in reactions which produce unwanted heavier alkylbenzenes.

For example, the xylenes can react to produce unwanted ethylbenzene by the following reaction:

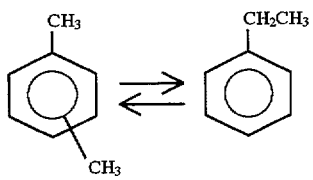

As explained in greater detail elsewhere herein, the present invention provides a process for obtaining p-dialkylbenzenes at alkylbenzene conversions of at least 10%, preferably at least about 15–25%, with a p-dialkylbenzene selectivity of greater than 85%, preferably at least 90%. The conversion rates and para-selectivity of this process are, accordingly, substantially enhanced over those observed in catalyst that has not been modified as described herein.

The alkylbenzene feedstock preferably includes about 50% to 100% alkylbenzene, more preferably at least about 80% alkylbenzene. Other compounds such as benzene and other alkyl-substituted benzenes may also be present in the toluene feedstock without adversely affecting the present invention.

The alkylbenzene feedstock may also be dried, if desired, in a manner which will minimize moisture entering the reaction zone. Numerous methods known in the art are suitable for drying the alkylbenzene charge for the process of the invention. These methods include percolation through any suitable desiccant, for example, silica gel, activated alumina, molecular sieves or other suitable substances, or the use of liquid charge dryers.

Operating conditions employed in the process of the present invention will affect the para-selectivity and alkylbenzene conversion. Such conditions include the temperature, pressure, space velocity, molar ratio of the reactants, and the hydrogen to hydrocarbon mole ratio ($H_2$/HC). For example, it has been observed that an increase in temperature can increase the activity of the modified catalyst. It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst.

A selectivated and steamed catalytic molecular sieve may be contacted with an alkylbenzene feedstock under conditions for effecting vapor-phase disproportionation. Conditions effective for accomplishing the high para-selectivity and acceptable alkylbenzene disproportionation conversion rates include a reactor inlet temperature of from about 200° C. to about 650° C., preferably from 350° C. to about 540° C.; a pressure of from about atmospheric to about 5000 psia, preferably from about 100 to about 1000 psia; a WHSV of from about 0.1 to about 20 $hr^{-1}$, preferably from about 2 to about 10 $hr^{-1}$; and a $H_2$/HC mole ratio of from about 0.05 to about 20, preferably from about 0.5 to about 6. This process may be conducted in either batch or fluid bed operation, with the attendant benefits of either operation readily obtainable. The effluent may be separated and distilled to remove the desired product, i.e., the para isomer, as well as other by-products. Alternatively, the appropriate fraction may be subjected to further separation, such as, in the case of xylenes, subjected to crystallization or the PAREX process to yield p-xylene.

The catalyst may be further modified in order to reduce the amount of undesirable by-products, such as, in the case of xylenes, ethylbenzene. The state of the art is such that the reactor effluent from standard toluene disproportionation typically contains about 0.5% ethylbenzene by-product. Upon distillation of the reaction products, the level of ethyl-benzene in the $C_8$ fraction often increases to between about 3% and 4%. This level of ethylbenzene is unacceptable for polymer grade p-xylene since ethylbenzene in the p-xylene, if not removed, degrades the quality of fibers ultimately produced from the p-xylene product. Consequently, ethyl-benzene content of the p-xylene product must be kept low. The specification for the allowable amount of ethylbenzene in the p-xylene product has been determined by the industry to be less than 0.3%. Ethylbenzene can be substantially removed by crystallization or by superfractionation processes.

In order to avoid the need for downstream ethylbenzene removal, the level of ethylbenzene by-product is advantageously reduced by incorporating a hydrogenation/dehydrogenation function within the catalyst, such as by addition of a metal compound such as platinum as described above. It will be appreciated by those skilled in the art that similar considerations apply to processes involving alkylbenzenes other than toluene.

The following Examples further illustrate the various features of the invention, and are not intended in any way to limit the scope of the invention, which is defined in the appended claims.

EXAMPLE 1

A 70%/30% w/w surfactant mixture was prepared by mixing 14.0 grams of TRITON®X-100 and 6.0 grams of TRITON®X-305.

EXAMPLE 2

A water/surfactant stock solution used to emulsify Dow silicone oil was prepared by mixing 17.0 grams of the 70%/30% surfactant mixture of Example 1 with 983.0 grams of distilled water. The resulting solution contained 1.7% surfactant in water.

EXAMPLE 3

An aqueous 65% silicone oil/water emulsion was prepared by mixing 111.42 grams of DC-510 (Dow phenylmethyl silicone oil) with 60 grams of water/surfactant solution prepared in Example 2. This solution was emulsified by mixing in a blender for 1 minute. This emulsion separated slightly upon sitting overnight. Mildly shaking the solution successfully restored the emulsion.

EXAMPLE 4

An aqueous 65% silicone oil/water emulsion was prepared by mixing 111.42 grams of DC-510 (Dow phenylmethyl silicone oil) with 60.0 grams of water/surfactant solution prepared in Example 2. This solution was emulsified by mixing in a blender for 2 minutes. This emulsion was stable after 1 month.

EXAMPLE 5

An aqueous 65% silicone oil/water emulsion was prepared by mixing 113.85 grams of DC-550 (Dow phenylmethyl silicone oil) with 61.3 grams of water/surfactant solution prepared in Example 2. This solution was emulsified by mixing in a blender for 2 minutes. This emulsion was stable after 1 week.

EXAMPLE 6

An aqueous 65% silicone oil/water emulsion was prepared by mixing 97.5 grams of DC-710 (Dow phenylmethyl silicone oil) with 52.5 grams of water/surfactant solution prepared in Example 2. This solution was emulsified by mixing in a blender for 2 minutes. This emulsion separated slightly upon sitting overnight. Mildly shaking the solution successfully restored the emulsion.

EXAMPLE 7

A diluted aqueous 6.5% silicone oil/water emulsion was prepared by mixing 32.5 grams of DC-710 (Dow phenylmethyl silicone oil) with 475.5 grams of the water/surfactant solution prepared in Example 2. This solution was emulsified by mixing in a blender for 2 minutes. This dilute emulsion separated slightly upon sitting overnight. Mildly shaking the solution successfully restored the emulsion.

EXAMPLE 8

0.63 grams of the silicone oil emulsion prepared in Example 3 was mixed with 0.87 grams of water surfactant solution prepared in Example 2. This mixture was contacted with 2.0 grams of 80%/20% HZSM-5/SiO$_2$ and heated under autogeneous pressure to 175° C. for 26 hours and cooled. The clear water layer was decanted off, the catalyst dried and calcined in air at 1° C./minute to 538° C./6 hours. SiO$_2$ uptake, measured by an increase in weight after calcination, was 9.5 wt. %.

EXAMPLE 9

0.87 grams of the silicone oil emulsion prepared in Example 3 was mixed with 1.13 grams of water surfactant solution prepared in Example 2. This mixture was contacted with 2.5 grams of 80%/20% HZSM-5/SiO$_2$ and heated under autogeneous pressure to 175° C. for 16 hours and cooled. The clear water layer was decanted off, the catalyst dried, and then calcined in air at 1° C./minute to 538° C. and held for 6 hours. SiO$_2$ uptake, measured by an increase in weight after calcination, was 10.4 wt. %.

Examples 10–13 reveal the benefit of applying the silicone agent in multiple rather than a single coating, in this case from hexane solution.

EXAMPLE 10

0.93 grams phenylmethyl silicone oil (DC-550) was dissolved in 40 cc hexane. To this solution was added 3.0517 grams HZSM-5 (SiO$_2$/Al$_2$O$_3$=26), with a crystal size of 0.2 micron, silica extrudate. The hexane was evaporated, and the extrudate was calcined in air at 538° C. overnight. The calcined extrudate was again impregnated with silicone solution, dried and recalcined. The finished extrudate contained 18% added silica.

EXAMPLE 11

This preparation was similar to Example 10, with the exception that 18% SiO$_2$ was applied in a single coating step.

EXAMPLE 12

0.77 grams DC-550 silicone oil was dissolved in 40 cc hexane. To this solution was added 3.0896 grams HZSM-5 (SiO$_2$/Al$_2$O$_3$=26), with a crystal size of 0.2 micron, silica extrudate. The hexane was evaporated, and the extrudate was calcined in air at 538° C. overnight. The calcined extrudate was again impregnated with silicone solution, dried and recalcined. The finished extrudate contained 20% added silica.

EXAMPLE 13

This preparation was similar to Example 12, with the exception that 20% SiO$_2$ was applied in a single coating step.

The catalysts of Examples 10–13 were tested for toluene disproportionation at 443° C., 500 psig, 4 WHSV, 2 H$_2$/HC, with the following results.

TABLE 1

| Example # | % Toluene Conversion | Xylene-p-selectivity |
|---|---|---|
| 10 | 33.0 | 64.1 |
| 11 | 33.0 | 48.0 |
| 12 | 21.1 | 61.0 |
| 13 | 32.5 | 48.8 |

EXAMPLE 14

This example adapts the findings of Examples 10–13 to emulsion coatings. 6.5 grams of the 65% silicone oil emulsion prepared in Example 3 was diluted to 65 grams with the water/surfactant mix prepared in Example 2. This diluted emulsion (6.5% oil/water) was circulated in recycle mode over a packed bed containing 20.0 grams of 80/20 NaZSM-5/SiO$_2$ for a total of 12 hours in 3 successive treatments with air calcinations to 538° C. between each impregnation. The final catalyst was NH$_4^+$ exchanged 3 times for 1 hour each with 1M NH$_4$NO$_3$ at room temperature. SiO$_2$ addition to the final catalyst measured by increase in weight was 6%.

EXAMPLE 15

Untreated 80/20 HZSM-5/SiO$_2$ catalyst with a crystal size of 0.2 micron was used to convert toluene at 446° C., 300 psig, and a hydrogen/hydrocarbon mole ratio of 2. Results in Table 2 show a para-xylene selectivity of 27.2% at 61.6% toluene conversion.

EXAMPLE 16

The catalyst prepared in Example 14 was used to convert toluene at 446° C., 300 psig, and a hydrogen/hydrocarbon mole ratio of 2. These results in Table 2 show a para-xylene selectivity of 55.4% at 29.6% toluene conversion.

EXAMPLE 17

A 4th aqueous silicone emulsion recycle air calcination was done on the catalyst prepared in Example 14. An additional 1% SiO$_2$ was added, as measured by the increase in catalyst Weight after calcination, and used to convert toluene at 425° C., 300 psig, and a hydrogen/hydrocarbon mole ratio of 2. Results in Table 2 show a para-xylene selectivity of 88.4% at 30.9% toluene conversion.

TABLE 2

| | Toluene Disproportionation Results | | |
|---|---|---|---|
| Example # | 15 | 16 | 17 |
| Temperature, °C. | 446 | 446 | 425 |
| Pressure, psig | 300 | 300 | 300 |
| $H_2$:HC (mole:mole) | 2 | 2 | 2 |
| WHSV, $hr^{-1}$ | 10 | 4 | 6 |
| % Toluene Conversion | 61.6 | 29.6 | 30.9 |
| p-xylene selectivity | 27.2 | 55.4 | 88.4 |

EXAMPLE 18

Silica modified HZSM-5 was prepared by a 2-step aqueous silicone emulsion impregnation procedure. To 1.13 grams phenylmethyl silicone emulsion (65% oil/0.6% surfactant) and 7.20 grams distilled water was added 4.50 grams HZSM-5 with a crystal size of 0.2 micron. Water was distilled using a rotovap. The product was program calcined in air at 1° C./minute to 538° C., then 6 hours at 538° C. The calcined catalyst weighed 4.89 g (7.98% added silica).

The above procedure was repeated using 1.23 grams phenyl-methyl silicone emulsion, 3.30 grams distilled water, and 2.46 grams of the silica modified HZSM-5. After water distillation and air calcination, the catalyst weighed 2.80 grams, corresponding to 19.6% added silica.

Coke trim-selectivation of this silica modified HZSM-5 catalyst (2.00 grams) was carried out at 579° C., 100 psig, and 0.5 WHSV using toluene feed. A mixture of nitrogen and hydrogen ($N_2/H_2=8$) was passed through the catalyst at 19.9 cc/minute. After 72 hours, the selectivation was terminated. The following table (Table 3) shows toluene conversion and p-xylene selectivity during trim-selectivation:

TABLE 3

| Time on Stream, Hrs. | Toluene Conversion, Wt. % | p-Xylene in Xylenes, Wt. % |
|---|---|---|
| 8 | 51 | 28 |
| 18 | 45 | 42 |
| 24 | 43 | 52 |
| 46 | 32 | 78 |
| 70 | 25 | 89 |

After trim-selectivation, the catalyst was tested under process conditions of 465° C., 500 psig, 3 WHSV, and a hydrogen/hydrocarbon ratio=2.0. At 23% toluene conversion, the p-xylene selectivity was a high 95.4%. The temperature was increased to 485° C. The toluene conversion increased to with p-xylene selectivity still high at 93.2%.

Trim-selectivation of silica modified HZSM-5 with organosilicon compounds produces catalysts giving very high 99+% p-xylene selectivity in toluene disproportionation processes. For catalysts with slightly lower p-xylene selectivity, trim-selectivation by -coking offers an alternative procedure. Since coke selectivation of HZSM-5 has been extensively studied, application of that selectivation experience to silica modified HZSM-5 appears viable.

While the invention has been described with reference to specific embodiments, it will be apparent that numerous variations, modifications, and alternative embodiments of the invention are possible, and accordingly all such variations, modifications, and alternative embodiments are to be regarded as being within the spirit and scope of the present invention as claimed.

What is claimed is:

1. A method for modifying a catalytic molecular sieve for shape selective hydrocarbon conversions, comprising exposing the catalytic molecular sieve to at least two ex situ selectivation sequences, wherein each ex situ selectivation sequence includes the steps of:
    a) contacting an intermediate pore catalytic molecular sieve with an aqueous emulsion comprising a silicon-containing selectivating agent, a surfactant, and an aqueous component; and
    b) calcining the contacted catalytic molecular sieve.

2. The method of claim 1, wherein the catalytic molecular sieve has been modified by between two and six ex situ selectivation sequences.

3. The method of claim 1, wherein the silicon-containing selectivating agent is selected from the group consisting of silicones, silicone polymers, silanes, and alkoxysilanes.

4. The method of claim 3, wherein the silicon-containing selectivating agent is selected from the group consisting of

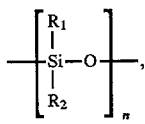

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and

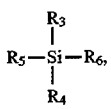

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

5. The method of claim 4, wherein the silicon-containing selectivating agent comprises phenylmethyl polysiloxane.

6. The method of claim 1, wherein the surfactant is a non-ionic surfactant selected from the group consisting of alcohol, alkylphenol, and polyalkoxyalkanol derivatives; glycerol esters; polyoxyethylene esters; anhydrosorbitol esters; ethoxylated anhydrosorbitol esters; natural fats, oils, waxes and ethoxylated esters thereof; glycol esters; polyalkylene oxide block co-polymer surfactants; poly (oxyethylene-co-oxypropylene) non-ionic surfactants; and mixtures thereof.

7. The method of claim 6, wherein the surfactant is an α-[4-(1,1,3,3-tetramethylbutyl)phenyl]-ω-hydroxypoly (oxy-1,2-ethanediyl).

8. The method of claim 7, wherein the surfactant is octoxynol-9.

9. The method of claim 1, wherein the aqueous component consists essentially of water.

10. The method of claim 1, wherein the aqueous component comprises water and a compound or a mixture of compounds selected from the group consisting of inorganic salts, alcohols having between 1 and 18 carbons, glycols, ethers, neutral or charged sulfoxides, neutral or charged amines, aldehydes, ketones, thiophenes, furans, and pyrroles.

11. The method of claim 1, further comprising the step of steaming the modified catalytic molecular sieve.

12. The method of claim 1, further comprising the step of in situ trim-selectivating the modified catalytic molecular sieve.

13. The method of claim 12, wherein the in situ trim-selectivating step comprises contacting the modified catalytic molecular sieve with a thermally decomposable organic compound selected from the group consisting of paraffins, cycloparaffins, olefins, cycloolefins, alkyl-substituted benzenes, aromatics, alcohols, aldehydes, ethers, ketones, phenols, heterocyclics, and mixtures thereof, at a temperature in excess of the decomposition temperature of the thermally decomposable organic compound.

14. The method of claim 12, wherein the in situ trim-selectivating step comprises contacting the modified catalytic molecular sieve with a reaction stream comprising an alkyl-substituted benzene and a second selectivating agent, at reaction conditions for shape selective disproportionation of the alkyl-substituted benzene.

* * * * *